US012748096B2

(12) United States Patent
Campbell et al.

(10) Patent No.: US 12,748,096 B2
(45) Date of Patent: Sep. 29, 2026

(54) FERTIGATION FEED SENSOR SYSTEM

(71) Applicant: ADDIUM, INC., Pullman, WA (US)

(72) Inventors: Gaylon S. Campbell, Pullman, WA (US); Scott H. Campbell, Pullman, WA (US); Kai Gaylon Campbell, Pullman, WA (US); Jon C. Hodgson, Springfield, MO (US); Robert Dale Agnes, Moscow, ID (US)

(73) Assignee: Addium Inc., Pullman, WA (US)

( * ) Notice: Subject to any disclaimer, the term of this patent is extended or adjusted under 35 U.S.C. 154(b) by 143 days.

(21) Appl. No.: 18/656,390

(22) Filed: May 6, 2024

(65) Prior Publication Data

US 2025/0341509 A1 Nov. 6, 2025

(51) Int. Cl.

| | |
|---|---|
| ***G01N 27/06*** | (2006.01) |
| ***A01G 9/24*** | (2006.01) |
| ***A01G 9/26*** | (2006.01) |
| ***A01G 27/00*** | (2006.01) |
| ***G01N 27/22*** | (2006.01) |
| ***G01N 33/24*** | (2006.01) |

(52) U.S. Cl.

CPC ........... *G01N 33/245* (2024.05); *A01G 9/247* (2013.01); *A01G 27/003* (2013.01); *A01G 27/005* (2013.01); *A01G 27/008* (2013.01); *G01N 27/06* (2013.01); *G01N 27/221* (2013.01); *G01N 27/223* (2013.01); *A01G 9/26* (2013.01)

(58) Field of Classification Search

CPC .... G01N 33/245; G01N 27/06; G01N 27/221; G01N 27/223; A01G 9/247; A01G 27/003; A01G 27/005; A01G 27/008; A01G 9/26

USPC .............................. 324/500, 600, 76.11, 689

See application file for complete search history.

(56) References Cited

U.S. PATENT DOCUMENTS

| | | | | |
|---|---|---|---|---|
| 2010/0332039 A1 | 12/2010 | Danieli | | |
| 2011/0144812 A1* | 6/2011 | Davis | G01F 23/24 700/281 | |
| 2020/0267917 A1* | 8/2020 | Hulday | A01G 25/167 | |
| 2021/0015056 A1* | 1/2021 | Main | A01G 27/008 | |

(Continued)

FOREIGN PATENT DOCUMENTS

KR 20180059522 A 6/2018

OTHER PUBLICATIONS

International Search Report and Written Opinion from International Application No. PCT/US2025/027791, dated Oct. 30, 2025.

*Primary Examiner* — Giovanni Astacio-Oquendo
*Assistant Examiner* — Trung Q Nguyen
(74) *Attorney, Agent, or Firm* — Dorsey & Whitney LLP

(57) ABSTRACT

A fertigation sensor system includes a first sensor system and a second sensor system. The first sensor system includes a first container configured to collect a feed solution originating from a fertigation source, the feed solution including water and fertilizer at a target ratio of concentration of water to fertilizer and a first sensor disposed in the first container. The second sensor system includes a second container configured to collect the feed solution originating from the fertigation source and a second sensor disposed in the second container. The sensor systems are usable to determine volumetric flow rates and electrical conductivity and permittivity of feed solution before and after being provided to one or more plants, thereby providing data indicating plant development and growth conditions.

19 Claims, 10 Drawing Sheets

(56) References Cited

U.S. PATENT DOCUMENTS

| | | | | |
|---|---|---|---|---|
| 2021/0173369 | A1* | 6/2021 | Lung | A01G 25/16 |
| 2021/0227761 | A1* | 7/2021 | Redman | A01C 23/042 |
| 2023/0036580 | A1* | 2/2023 | Sabti | B05B 7/32 |
| 2023/0172098 | A1* | 6/2023 | Geerligs | A01C 23/007 47/48.5 |
| 2023/0380337 | A1* | 11/2023 | Yun | A01G 9/247 |

* cited by examiner

FERTIGATION FEED SENSOR SYSTEM

BACKGROUND

When crops are produced outdoors, nutrients and water are largely supplied to the crop by the soil in which the crop is growing. In controlled agricultural environments, crops can be grown in substrates like stone wool, coconut coir, vermiculite, or peat moss. These substrates have little, if any, nutrients to supply to the plants, so the needed nutrients are usually supplied with the irrigation water. The plant takes up the water it needs for transpiration from the substrate, and the water in the substrate is then replaced by irrigation. In that process, the plant also takes up the nutrients it needs from the irrigation, if they are available. If the concentration of nutrients in the irrigation water exceeds that needed for plant growth, then the excess will build up in the substrate, eventually reaching levels that could harm the plant. On the other hand, if the concentration is too low to meet the needs of the growing plant, the concentration in the substrate will decrease and plant growth could be limited by the availability of nutrients. A grower can supply both water and nutrients at rates that exceed the highest plant usage rates, but then the excess water and nutrients drain out of the substrate, thereby increase the cost of production due to the waste.

Mass balance principles are a cornerstone for efficient fertilizer use and can be utilized to optimize plant nutrition without discarding or leaching solution. Water removed by transpiration can be restored with solution that replaces the nutrients that were taken up with the water. Nutrients are supplied to the plant with the irrigation water, and are lost to the system through drainage. The amounts of irrigation and drainage, multiplied by the concentrations of nutrients in each stream, determine the inputs and losses of nutrients to the system. Nutrients are taken up by the plant to satisfy its needs, but nutrients in excess of the plant's needs can accumulate in the substrate. The rate of uptake of nutrients by the plant is determined by the rate of photosynthesis of the plant, but the rate of supply of nutrients is determined by the transpiration rate, since that determines the amount of irrigation water supplied. Transpiration and photosynthesis are proportional to each other, so a correct nutrient balance for the crop is closely tied to factors that determine transpiration rate.

SUMMARY

Embodiments disclosed herein include systems, assemblies, and methods for a fertigation sensor system. In some embodiments, a fertigation sensor system can include a first sensor system and a second sensor system. In an example, the first sensor system can include a first container configured to collect a feed solution originating from a fertigation source, the feed solution including water and fertilizer at a target ratio of concentration of water to fertilizer and a first sensor disposed in the first container. In an example, the second sensor system can include a second container configured to collect the feed solution originating from the fertigation source, and a second sensor disposed in the second container. In some examples, the feed solution can be respectively distributed to the first sensor system and the second sensor system from the fertigation source via a first feed inlet and a second feed inlet. The first feed inlet and the second feed inlet can be configured to provide the feed solution at equal volumetric flow rates. In some examples, the first feed inlet and the second feed inlet have the same target ratio of concentration of water to fertilizer.

In at least one example, the first sensor can include an electrical conductivity and permittivity sensor having at least one prong positioned extending upward from a bottom wall of the first container. In an example, the at least one prong includes two electrodes spaced apart from each other within the first container. In some examples, the two electrodes can be laterally spaced apart from each other.

In some examples, the first container can include a first automatic drainage system and the second container comprises a second automatic drainage system. In an example, the second container can be configured to collect leachate from a plant container after the plant is provided the feed solution.

In some examples, a sensor station can include a receptacle configured to hold a feed solution, a conductivity and permittivity sensor, and a drain. In an example, the conductivity sensor can include at least two prongs disposed in the receptacle. In some examples, the drain can be configured to remove the feed solution from the receptacle when a predetermined amount of feed solution is present in the receptacle. In an example, the drain can include a siphon.

In some examples, the conductivity and permittivity sensor can be connected to a controller configured to periodically measure and record the conductivity and permittivity of the feed solution. In an example, the at least two prongs of the conductivity sensor can extend from a bottom surface of the receptacle. In some examples, the at least two prongs can include electrodes that terminate at or below the top of a solution receiving chamber defined in the receptacle. In an example, the sensor station can further include a pH probe disposed in the receptacle.

In at least one example, a method of determining a fertigation feed properties can include establishing a feed sensor system by feeding a first container with a feed solution that includes water and fertilizer at a target ratio of concentration of water to fertilizer, the first container including a feed sensor. In an example, the method can further include establishing a runoff sensor system by feeding a plant container with the feed solution and configuring a second container to receive runoff from the plant container, the second container including a runoff sensor. In some examples, the method also includes measuring a volumetric flow rate of the feed solution and the runoff and measuring electrical properties of the feed solution with the feed sensor and electrical properties of the runoff with the runoff sensor.

In some examples, the method can further include determining, for the feed solution and the runoff, at least one of: a feed solution balance value or a salinity value. In an example, measuring a volumetric flow rate of the first inlet line can include periodically draining the first container and tracking drainage events over time. In some examples, tracking drainage events can include measuring the electrical properties in the first container and correlating the electrical properties to a fluid level in the first container. In an example, measuring the electrical properties of the feed solution can include measuring at least the electrical conductivity and feed solution with the feed sensor. In some examples, the method can further include modifying fertigation parameters based on the volumetric flow rate and the electrical property measurements.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the present disclosure, wherein identical reference numerals refer to identical or similar elements or features in different views or embodiments shown in the drawings.

DETAILED DESCRIPTION

Embodiments disclosed herein are related to assemblies, systems, and methods of determining feed properties for a fertigation system. The assemblies, systems, and methods of determining feed properties include a fertigation sensor system for controlling nutrition in an indoor or other controlled environment agriculture system using sensor-based feeding systems. In some examples, the fertigation sensor system can be attached to a plant watering zone without interfering with the installed fertigation and irrigation systems, which can subsequently lower the costs of installing the monitoring system onto present plant fertigation systems.

In some examples, the fertigation sensor system can be used to help determine the irrigation flow rate of a feed solution at both an inlet (e.g., an inflow point directly providing solution to a zone of plants such as a table or row of plants) and/or runoff of a plant (e.g., receiving the runoff or leachate of a plant within the zone, table, or row) by tracking the rate at which a dielectric sensor station is filled and emptied over time. Because of its precision, fertigation may require less water and fertilizer than traditional application methods and can reduce the leaching of chemicals into the water supply. In addition to reducing water and fertilizer use, the need for herbicides and pesticides is also reduced due to the increased health of the plant system. The fertigation sensor system can also be used to determine the fertilizer content of the inlet and runoff solution via electrical property measurements taken during sensor operation. Conductivity and permittivity measurements, taken periodically, can be compared to determine whether to change the inlet flow rate or fertilizer content of the feed solution for a group of plants. Accordingly, with just two sensor systems installed, the feed and runoff status for an entire zone or group of plants can be tracked and actively managed. This may greatly reduce the total number of sensor stations needed to achieve plant growth outcomes that would otherwise require tens of sensors, such as a sensor per plant.

Figure 1:
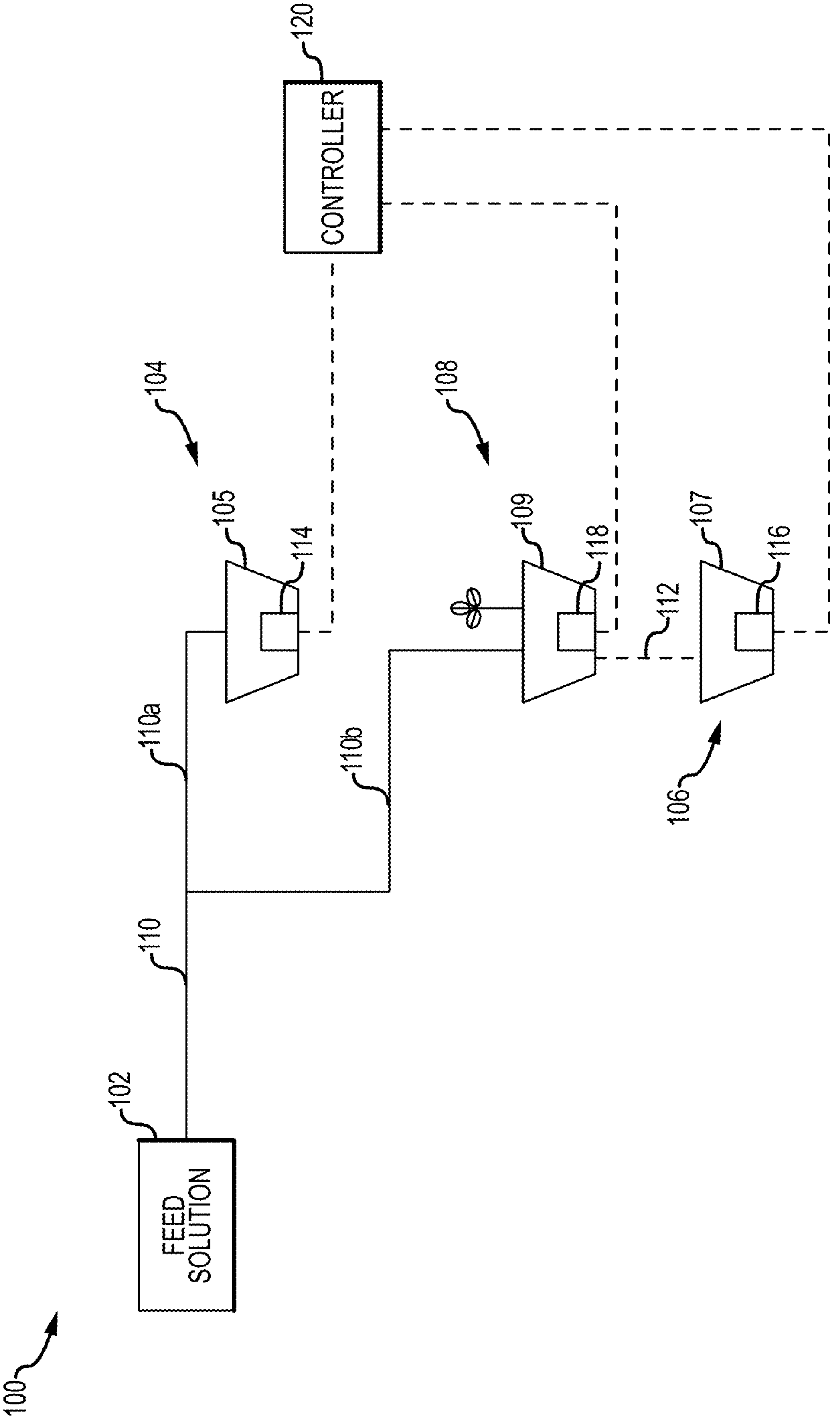
FIG. 1 is a flow diagram of a fertigation sensor system.

FIG. 1 is a flow diagram of a fertigation system 100. In an example, the fertigation system 100 is configured to direct a feed solution 102 originating from a fertigation source to a first sensor system 104 and a second sensor system 106. In some examples, the fertigation system 100 can be configured to analyze and evaluate the feed solution for improving the growth and/or the yield of a plant system. In an example, the feed solution 102 originating from a fertigation source can include at least one of water and fertilizer, and usually both. The feed solution 102 can include nutrients and/or fertilizer dispersed uniformly within the water to provide a well-mixed nutrient solution that can be injected directly into or dispersed onto a substrate (e.g., soil) and enable and/or improve plant growth in controlled environments. In some examples, the feed solution 102 can include at least one of ammonium nitrate, urea ammonium nitrate, calcium nitrate, ammonium thiosulfate, potassium chloride, potassium sulfate, potassium nitrate, phosphoric acid, sulfuric acid, and/or other compounds as requisite for the intended plant species in a particular zone being fed and monitored. In some examples, the feed solution can include water and fertilizer at a predetermined target ratio concentration of water to fertilizer.

In some examples, the first sensor system 104 can include a first container 105 configured to collect the feed solution 102. The first container 105 can include any suitable receptacle that includes a material configured to retain water and the feed solution 102, such as, for example, a container shaped as a cup, bucket, spoon receptacle, tilting receptacle, or box. See also FIGS. 2A-2E. The second sensor system 106 can include a second container 107 configured to collect the feed solution 102 via a third container 109. The second container 107 can be configured similarly to the first container 105, as explained in further detail elsewhere herein. In some embodiments, the third container 109 can be a grow container, such as a plant pot, planter box, substrate, polybag, basket, tray, a similar type of container, or combinations thereof.

In some examples, the fertigation system 100 can further include a third sensor system 108. The third sensor system 108 can also include the third container 109, and the third container 109 can be configured to be fed with the feed solution 102 along with the first container 105. In some examples, the first sensor system 104 and the third sensor system 108 can be simultaneously fed from a shared feed line 110 that includes the feed solution 102 having the water and fertilizer at a target ratio of concentration of water to fertilizer. In other words, the same feed line 110 can be the source of the feed solution 102 to both the first sensor system 104 and the third sensor system 108. In some examples, the feed line 110 can include two separate feed lines (e.g., 110*a*, 110*b*) originating from the same feed solution source, with each feed line configured to provide the feed solution 102 at equal volumetric flow rates. In some examples, each feed line can be configured to provide the same target ratio of concentration of water to fertilizer. Each feed line can also have a respective inlet or outlet to ensure that the volumetric flow rates in each feed line are equal. In some examples, the feed solution 102 can be applied to the first sensor system 104 and/or the third sensor system 108 using drip irrigation, a soaker hose, or similar irrigation technique. For each irrigation supply line, flow may be controlled so that the same flow rate of water or fertilizer solution is emitted from each supply line.

In some examples, the second sensor system 106 can be fed from a feed line 112 that includes a runoff from the third sensor system 108. In some embodiments, the feed line 112 can include a funnel or similar collector configured to aggregate fluid drained or otherwise passing out of the third container 109 and/or plants, soils, and substrates within the third container 109 and to direct and provide the fluid into the second container 107. In some examples, the fluid aggregated into the third container 109 can be referred to as runoff of the third container 109. As used herein, the term “runoff” includes the drainage and/or leachate of water, fertilizer, feed solution, or fluid from an area, receptacle, or container. In some examples, the third sensor system 108 can include a plant system disposed in or on the third container 109. The plant system can include a plant or plurality of plants of a singular or varied species. In other words, the second container 107 of the second sensor system 106 can be configured to collect leachate from a plant container. In some examples, the third sensor system 108 having the third container 109 can include a soil. For purposes of this disclosure, the term “soil” can include a body of solids (e.g., minerals and organic matter), liquid, and gases that occurs naturally on land surfaces, occupies space, and is characterized by the ability to support rooted plants in a natural or a controlled environment. In some examples, soil can include natural and/or synthetic material, for example: stone wool, coconut coir (“coco coir”), vermiculite, peat moss, organic remains, clay, and rock particles.

In some examples, the first container can include a first automatic drainage system and the second container comprises a second automatic drainage system. The automatic drainage systems included in the first container and the second container are described in greater detail below.

In some examples, the first container 105 can also include a first sensor 114 (e.g., an electrical conductivity sensor, a permittivity sensor, dielectric sensor, or complex dielectric sensor (CDS)) disposed therein. In some embodiments, the sensor can comprise a complex dielectric sensor as described in U.S. Pat. No. 11,415,612, issued 16 Aug. 2022, the entire disclosure of which is hereby incorporated by reference. The first sensor 114 is configured to measure the electrical properties, including electrical conductivity and permittivity, of the feed solution 102 collected within the first container 105 of the first sensor system 104. In an example, the sensor 114 can provide a measurement of the nutrient and/or fertilizer concentration in the feed solution 102 and a volume of irrigation water being fed to the first container 105. In some examples, the volume of irrigation water multiplied by the concentration of nutrients in the irrigation water can be referred to as the amount of nutrients applied. In some examples, at least some components of the first sensor 114 can be integrated into the first sensor system 104 and/or integrated into the first container 105.

Similarly, in some examples, the second container 107 can include a second sensor 116. The second sensor 116 can comprise a same type of sensor as the first sensor 114. The second sensor 116 can be configured to measure the electrical properties, including conductivity and permittivity, of the runoff from feed line 112 within the second sensor system 106. In some examples, at least some components of the second sensor 116 can be integrated into the second sensor system 106 and/or integrated into the second container 107. The volume of drainage, multiplied by the concentration of nutrients in the drainage, can be tracked using the first and second sensors 114, 116 to determine the amount of nutrients lost from the system. Any differences between the nutrients provided via the feed line 110 to the first sensor system 104 and the nutrients measured at the second sensor system 106 can represent the amount of nutrients taken up by the plant system, e.g., plants supported by the third container 109, as long as measurements are taken over a sufficient span of time to filter out or average out temporary fluctuations in water and nutrient storage by the substrate.

In some examples, the third container 109 can include a third sensor 118 disposed therein. In some examples, the third sensor 118 can measure the electrical conductivity and permittivity of material within or supported by the third container 109. In some examples, the third sensor 118 can include a soil sensor or a sensor similar to the first and second sensors. For example, the third sensor 118 can include a soil moisture sensor that uses capacitance to measure dielectric permittivity of the surrounding medium. In soil, a dielectric permittivity is a function of the water content. The sensor can be configured to create a voltage proportional to the dielectric permittivity, and therefore identify the water content of the soil.

In some examples, any or all of the sensors 114, 116, and 118 can be operationally coupled to a controller 120. The controller 120 can comprise a comparative device that receives an input signal from the sensors, compares this value with that of a predetermined control point value (e.g., a set point), and determines the appropriate amount of output signal required by the final control element to provide corrective action within a control loop. For example, at least one of the sensors installed at the containers can send an input signal to the controller 120. The input signal can indicate a water content (e.g., volume) or electrical conductivity measured at a container. At a predetermined set interval, the controller can compare this signal to a predefined set point. If the input signal deviates from the set point, the controller sends a corrective output signal to a control element (e.g., an input flow valve). In some examples, the controller 120 includes a computer and other components, described in greater detail below, configured to measure and record the conductivity, permittivity, and/or volume of the feed solution 102 and to provide status feedback of the components in the fertigation system 100.

Figure 2A:
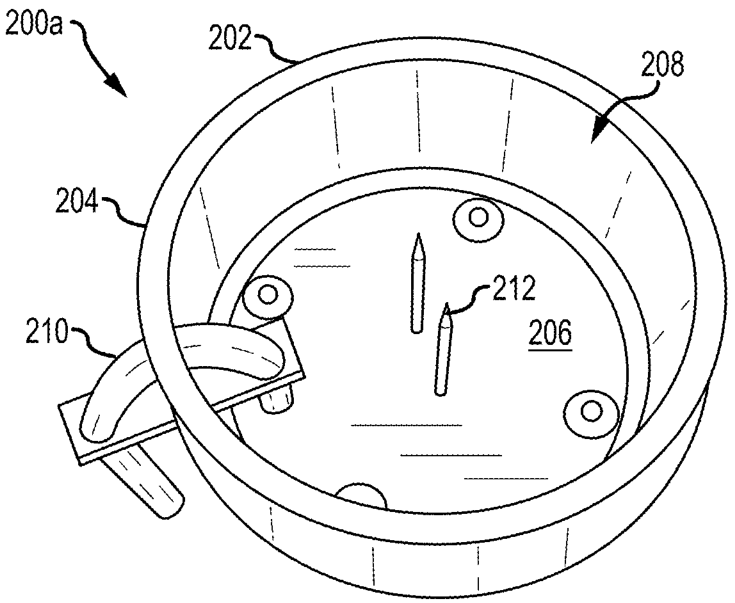
FIG. 2A is an isometric view of a dielectric sensor station.

FIG. 2A is an upper perspective view of a dielectric sensor station **200*a* for monitoring fertigation conditions for controlled environmental crops, according to an embodiment. In an example, the dielectric sensor station 200*a* can be included in at least one of the first sensor system 104, the second sensor system 106, and/or the third sensor system 108 shown in FIG. 1. In an example, the dielectric sensor station 200*a* includes a receptacle 202 configured to hold a feed solution. In some examples, the receptacle 202 can define a receiving chamber defined by a side wall 204, a bottom wall 206, and at least one opening 208 (e.g., a top opening). In an example, the dielectric sensor station 200*a* also includes a drain 210** or fluid outlet system.

In some examples, the receptacle 202 can include a plastic material or any other suitable fluid impermeable barrier. The receptacle 202 may be formed of any suitable fluid impermeable material(s), such as a fluid impermeable polymer (e.g., silicone, polypropylene, polyethylene, polyethylene terephthalate, a polycarbonate, etc.), a metal, natural rubber, another suitable material, or combinations thereof. As such, the receptacle 202 substantially prevents water and/or a feed solution from passing through the receptacle 202.

In some examples, the dielectric sensor station **200*a* can further include a sensor 212 disposed within an interior portion of the receptacle 202. The sensor 212 can be configured to detect a property related to the volume or mass of the fluid in the receptacle 202 and also to detect a property related to the electrical conductivity of the fluid in the receptacle 202. In some examples, the sensor 212** can include at least one prong-shaped (or differently-shaped)

electrode positioned extending upward from the bottom wall 206 of the receptacle 202. In some examples, the at least one prong includes at least two electrodes spaced apart from each other within the receptacle 202. In at least one example, the two electrodes are vertically oriented and laterally spaced apart from each other within the receptacle 202. The sensor 212 can be a sensor 114, 116, 118 discussed in connection with FIG. 1.

Figure 2B:
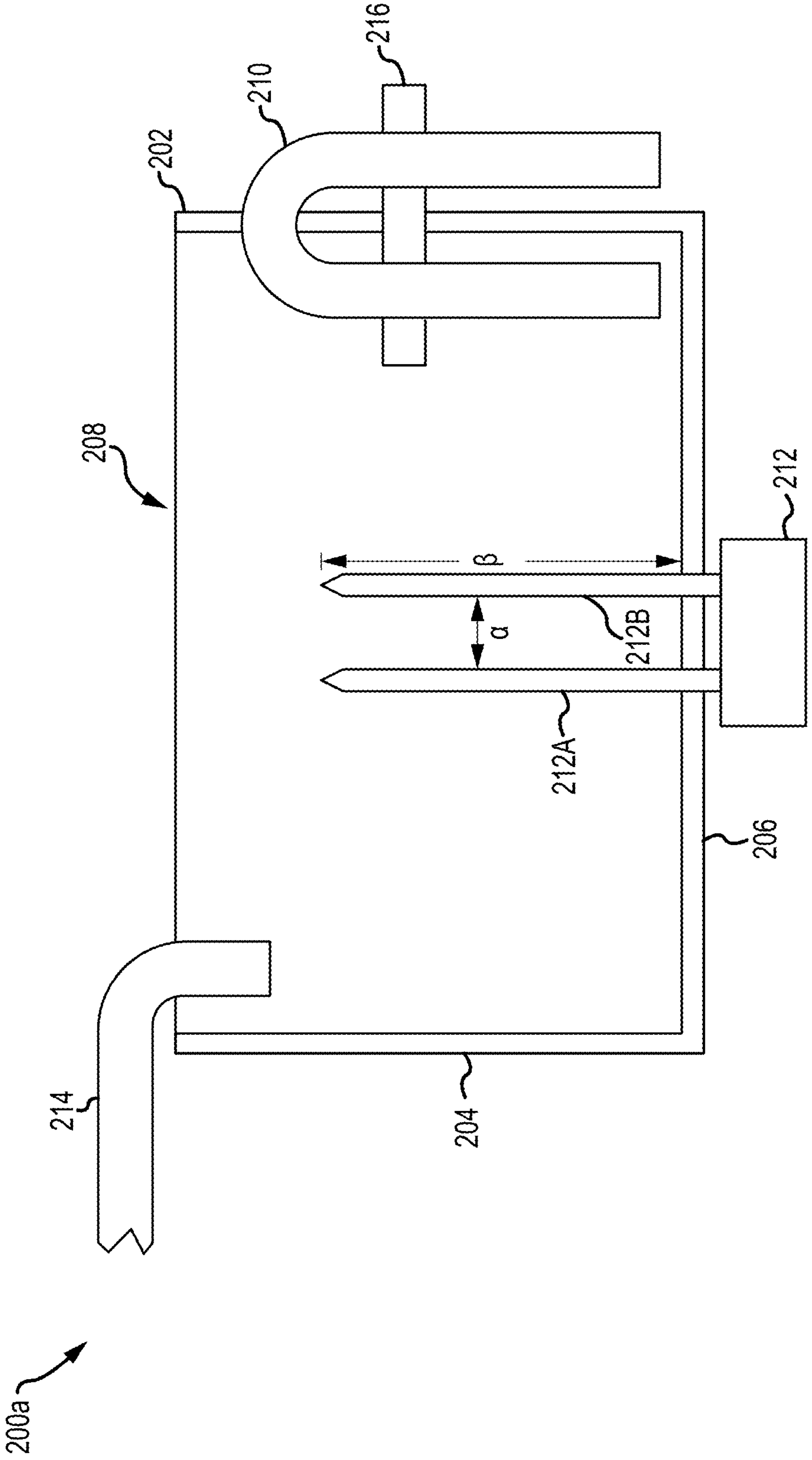
FIG. 2B is a schematic side view of the dielectric sensor station of FIG. 2A.

FIG. 2B is a side cross-sectional view of the dielectric sensor station 200*a* with a feed inlet 214 added. As discussed above, the container or receptacle 202 includes a side wall 204, a bottom surface 206, at least one opening 208, and a drain 210. As shown in side view in FIG. 2A, the sensor 212 can include a conductivity and permittivity sensor having at least two prongs disposed in the receptacle 202. In an example, the first prong 212A and the second prong 212B extend upward into the receptacle 202 from the bottom surface 206 of the receptacle 202.

In some examples, the at least two prongs 212A, 212B can include electrodes that terminate at or below the top edges of the solution receiving chamber defined in the receptacle 202. In other words, the at least two prongs 212A, 212B can each have an equal length β, as measured extending up from the bottom surface 206 of the receptacle 202. In some embodiments, the length β can be about equal to (or greater than) the height of the sidewalls 204 of the receptacle 202. In some embodiments, the length β can be about equal to a height within the receptacle 202 wherein, as fluid is collected in the receptacle 202 from the inlet 214, the fluid is automatically drained from the receptacle 202. Thus, the length β can meet or exceed the height at which drain 210 drains the receptacle 202. In this manner, the electrodes of the sensor 212 can be configured to estimate or detect the quantity and/or conductivity of fluid in the container over time, including at times when the contained fluid is at or near its maximum pre-drained volume. In some examples, the length β of the electrodes can be between about 5 cm and about 10 cm. In some examples, the electrodes can include a length less than 12 cm. In other examples, the electrodes can include a length less than 10 cm, less than 8 cm, or less than 6 cm. In some examples, the length of the electrodes can be within a range extending between about 5 cm and about 12 cm. Other ranges can include between about 5 cm and about 6 cm, between about 6 cm and about 7 cm, between about 7 cm and about 8 cm, between about 8 cm and about 9 cm, between about 9 cm and about 10 cm, between about 10 cm and about 11 cm, or between about 11 cm and about 12 cm.

In an example, the two prongs 212A, 212B, are set at a fixed lateral distance a apart from each other. In some examples, a can be a dimension between about 0.5 cm and about 4 cm. In some examples, the distance a between the electrodes can include a length less than 5 cm. In other examples, the distance a between the electrodes can include a length less than 4 cm, less than 3 cm, or less than 2 cm. In some examples the distance a between the electrodes can be in a range extending between about 0.5 cm and about 6 cm. Other ranges can include a range between about 1 cm and about 2 cm, a range between about 2 cm and about 3 cm, a range between about 3 cm and about 4 cm, a range between about 4 cm and about 5 cm, or a range between about 5 cm and about 6 cm.

The conductivity of a solution can be referred to as a measure of the solution's ability to conduct electricity, and can be directly related to the concentration of ions in the solution, and the ions in the solution are related to the concentration of fertilizers and other chemicals in water provided to the system 100. The sensor 212 can include the two electrodes (212A and 212B) that are slowly covered by and immersed in the solution provided by the inlet 214. An electrical current passes between the electrodes or an electrical potential between the electrodes is measured, and the conductivity of the solution may then be determined based on measured current or potential in the solution. In some examples, the electrodes (212A and 212B) can comprise a conductive material such as platinum, gold, stainless steel, or graphite. The type of electrode material and the design of the electrode can affect the accuracy and precision of the conductivity measurement.

In some embodiments, the sensor 212 can include a reference electrode and a measuring electrode. The reference electrode is used to provide a stable reference voltage for the measurement, while the measuring electrode is used to detect the current flowing through the solution. The conductivity of the solution is determined based on the amount of current that flows through the solution. In some examples, the sensor 212 can be connected to a controller configured to measure and record the conductivity of the feed solution periodically.

The conductivity measurement can then be used to calculate the concentration of ions in the solution using the appropriate equations and conversion factors. Electrical conductivity can be used to monitor the concentration of nutrients in the feed solution, substrate, and runoff. While the relationship between nutrient concentration (g/kg) and electrical conductivity can vary, depending on the makeup of the solution, a linear relationship exists between electrical conductivity and nutrient concentration. Thus, if the electrical conductivity of any particular concentration can be determined, the electrical conductivity of any other concentration can also be derived.

The permittivity of a solution can be referred to as a measure of the solution's ability to store electrical energy. Materials that have no free charge carriers such as ions or electrons may still appear to pass current when a voltage is applied. The sensor 212 can include the two electrodes (212A and 212B) that are slowly covered by and immersed in the solution provided by the inlet 214. An electrical current passes between the electrodes or an electrical potential between the electrodes is measured, and the permittivity of the solution may then be determined based on measured current or potential in the solution. A solution or substrate with a high permittivity polarizes more in response to an applied electric field than a solution or substrate with low permittivity, thereby storing more energy. In some examples, the sensor 212 can be connected to a controller configured to measure and record the permittivity of the feed solution periodically.

The permittivity measurement can then be used to calculate the volume of the solution using the appropriate equations and conversion factors. Permittivity can be used to monitor the volume of the solution or water content in the feed solution, substrate, and runoff. While the relationship between permittivity and water content can vary, depending on the makeup of the solution, a relationship exists between the permittivity of a solution and the volume. Thus, if the permittivity of any particular substrate can be determined, the volume of solution in a container can be derived based on the correlation.

In an example, the dielectric sensor station 200*a* can also include a feed inlet 214. The feed inlet 214 can be connected to a feed line (e.g., feed line 110 or feed line 112) described above. In some cases, the feed inlet 214 can include two separate feed lines originating from the same feed solution source, with each feed line being configured to provide the feed solution into the receptacle 202 at substantially equal volumetric flow rates. The feed inlet 214 can include one or more valves or other control mechanisms to allow the user to manage the rate of flow of fluid into the receptacle 202 of the sensor station 200*a*. The feed inlet 214 may be configured to gradually fill the receiving chamber defined in the receptacle 202 at the same rate at which fertigation fluid is provided to plants (e.g., a plant of third container 109).

To control the fluid level retained in the receiving chamber defined in the receptacle 202, the dielectric sensor station 200*a* may also include a fluid outlet or drain 210. In some examples, the drain 210 can be configured to remove the feed solution from the receptacle 202 in response to a predetermined amount of feed solution being accumulated and present in the receptacle 202. The drain 210 can include an automatic drainage system. As shown in FIGS. 2A-2B, the drain 210 includes a siphon tube. The siphon of the drain 210 can have a first end positioned at a low point within the receptacle 202, e.g., near the bottom wall 206, a middle section positioned above the bottom wall, e.g., near or at the same elevation as the top ends of the electrodes (212A, 212B), and a second end positioned external to and extending below the bottom of the receptacle 202. Therefore, the drain 210 will allow fluid to accumulate within the receptacle 202 until it begins to exceed the elevation of the middle section of the tube, at which time all or nearly all of the fluid in the receptacle 202 will be siphoned out of the chamber. Thus, in some examples, a drain 210 that includes a siphon can rely on gravity to periodically automatically evacuate the receptacle 202. This means the receptacle 202 will cyclically fill, drain, fill again, and drain again, over and over, indefinitely, as long as fluid is continuously provided by the inlet 214. In some configurations, the siphon drain includes a stabilizer 216 that retains the parts of the siphon in the proper predetermined arrangement relative to the rest of the receptacle 202 to ensure the siphon operates as designed. In some examples, the stabilizer 216 can be adjusted manually to ensure correct drain operation.

Figure 2C:
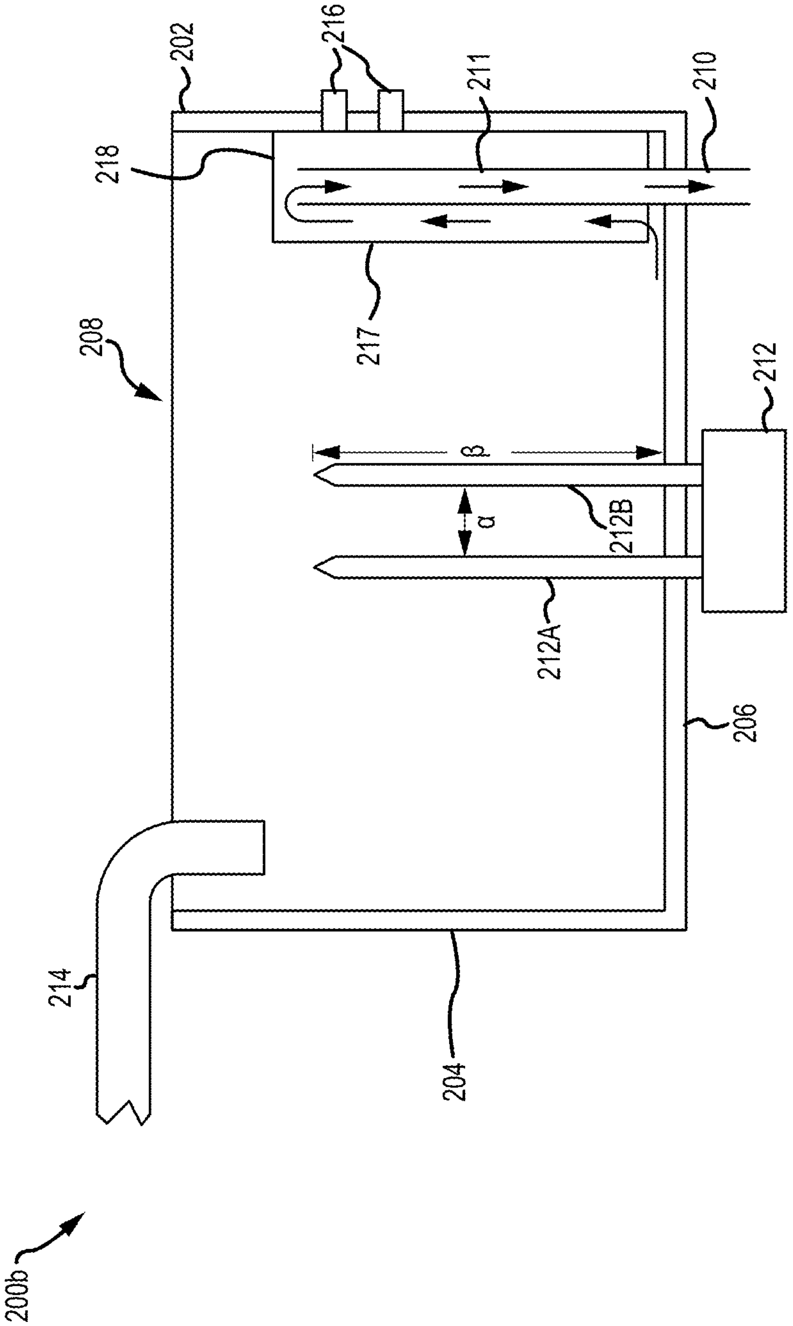
FIG. 2C is a side view of a dielectric sensor station.

FIG. 2C is a side cross-sectional view of a dielectric sensor station 200*b* illustrating features that can be implemented into other sensor stations described herein. As discussed above, the container or receptacle 202 includes a side wall 204, a bottom surface 206, at least one opening 208, and a drain 210. Similar to the embodiment of FIGS. 2A-2B, the drain 210 can include an automatic drainage system. As shown in FIG. 2C, the drain 210 includes a bell, or Pythagorean, siphon 218. The bell siphon 218 of the drain 210 can have a first end of its bell top 217 positioned at a low point within the receptacle 202, e.g., near the bottom wall 206, and a second end at the top of standpipe 211 near or at the same elevation as the top ends of the electrodes (212A, 212B). The bell siphon 218 can leverage the forces of pressure and gravity, whereby as the container or receptacle 202 fills and the fluid level reaches the top of the drain standpipe 211 located inside the bell top 217 and sufficiently begins to flow through the drain standpipe 211, a low pressure area or partial vacuum will cause the feed solution to automatically flow through the siphon at the top of the drain standpipe 211 and out through the exit of the drain 210. The length from the bottom opening of the bell top 217 to the top of the drain standpipe 211 can be greater than the length from the bottom of the opening of the drain 210 to the top of the drain standpipe 211 to help with this effect. In some embodiments, the drain standpipe 211 can be concentrically positioned within the bell top 217, and in some cases, the standpipe 211 can be offset from the center of the bell top 217. The bell top 217 can be integrated into a sidewall 204 for stability and durability or can be free-standing and spaced apart from the sidewalls to increase the siphon flow rate when activated.

Thus, as the feed solution starts to drain out of the drain standpipe 211, the feed solution can accumulate within the bell top 217, pushing any air out through the standpipe 211. The resulting suction and low pressure in the bell top 217 leads to a pressure differential between the bell top 217 and the surrounding atmosphere, thereby initiating the siphon action. The siphon pushes out and drains the feed solution from the container or receptacle 202 rapidly through the drain standpipe 211 at a higher pressure until the feed solution level within the container or receptacle 202 is substantially empty due to reaching a base of the bell top 217 and air can once again enter the bell top 217 to stop the siphon flow.

Thus, as the feed solution level approaches the bell siphon 218 base, air can enter the bell through the opening at the bottom of the bell siphon 218, relieving the pressure difference between the bell top 217 and the atmosphere, which causes the siphon to break and halt the drain of the fluid. As the inlet 214 continues to input feed solution, once the level of feed solution reaches the top of the drain standpipe 211, the siphon will again initiate, and the drain cycle repeats.

Therefore, the drain 210 will allow fluid to accumulate within the receptacle 202 until it begins to exceed the elevation of the drain standpipe 211, at which time all or nearly all of the fluid in the receptacle 202 will be siphoned out of the chamber. In some configurations, the bell siphon 218 includes a stabilizer 216 that retains the parts of the siphon in the proper predetermined arrangement relative to the rest of the receptacle 202 to ensure the siphon operates as designed. In some examples, the stabilizer 216 can be adjusted manually to ensure correct drain operation. Furthermore, in some cases, the bell siphon 218 can be integrally formed with (e.g., molded from) the sidewalls 204 and/or bottom wall 206 of the receptacle 202. Embodiments using a bell siphon 218 can have a reduced lateral profile as compared to a tube siphon 210 shown in FIG. 2B since the bell siphon 218 is entirely positioned within the sidewalls 204 of the receptacle 202.

Figure 2D:
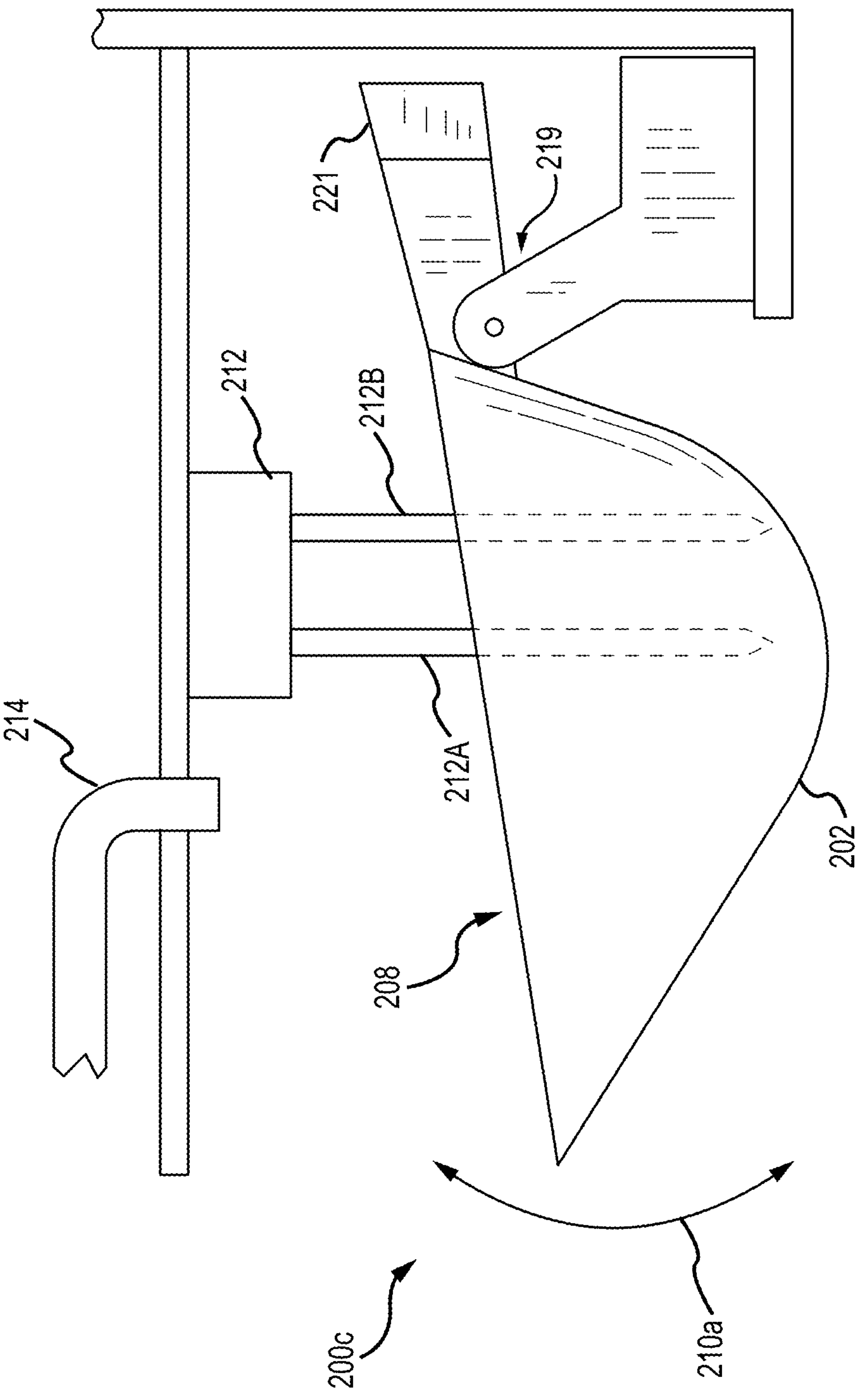
FIG. 2D is a side view of a dielectric sensor station.

FIG. 2D is a side view of a dielectric sensor station 200*c*, according to an embodiment. The dielectric sensor station 200*c* includes a receptacle 202 that may be referred to as a spoon receptacle or tilting receptacle. The spoon receptacle 202 includes an opening 208 and tilting drain functionality, as represented by arrow 210*a* in FIG. 2D. Similar to the embodiment of FIGS. 2A-2C, the receptacle 202 can be automatically drained. The top opening of the spoon receptacle 202 can be referred to as a drain since fluid can periodically, automatically flow out of the top opening, as explained below. As shown in FIG. 2D, the feed solution from inlet 214 can drop into and be collected by the spoon receptacle 202. The spoon receptacle 202 can have a first end connected at a hinge or lever 219. The spoon receptacle 202 uses a gravity-based tilting mechanism, wherein as the spoon receptacle 202 fills, the weight of the feed solution within the receptacle 202 overcomes a counterweight 221 at the hinge or lever 219, and the spoon receptacle therefore tips and tilts downward (as indicated by arrow 210*a*) so that the feed solution pours out of the spoon receptacle 202.

After the feed solution sufficiently drains out of the spoon receptacle 202, the counterweight 221 pulls the spoon receptacle 202 back to its initial position, and the feed solution can again accumulate within the receptacle 202. As shown in FIG. 2D, the sensor 212 can include a conductivity and permittivity sensor having at least two prongs configured to be disposed in the receptacle 202 as the receptacle 202 is filled by fluid. In an example, the first prong 212A and the second prong 212B extend downward into the receptacle 202 from a surface disposed over the receptacle 202 and through which the feed inlet 214 can extend. In some examples, the at least two prongs 212A, 212B can include electrodes that extend into a deepest portion of the spoon receptacle 202 and terminate prior to contacting an inner surface of the spoon receptacle 202, but within the spoon and below the top edge defined in the receptacle 202. The at least two prongs 212A, 212B can have respective lengths and positions relative to the receptacle 202 that allow the receptacle 202 to fully tilt and empty or fully fill without the receptacle 202 coming into contact with the prongs. The maximum depth of fluid accumulation in the receptacle 202 can provide a measurement, via the sensor 212, of the conductivity and permittivity of the fluid, and this information can be tracked over time to determine the flow rate of the fluid into the receptacle 202 and to determine the fertilizer content of the fluid, as described in greater detail in connection with other embodiments herein.

In some embodiments, the sensor station 200*c* can comprise multiple receptacles 202, such as, for example, two receptacles positioned on opposite sides of a pivot point, fulcrum, hinge, or lever (e.g., 219). Each receptacle can be filled independently, and one receptacle can act as a counterweight for the opposite receptacle as it is filled. Each receptacle can have its own sensor 212 and prongs 212A, 212B as well. Thus, the spoon receptacle embodiment of FIG. 2D can include two spoon receptacles that alternate between being filled and tilting to drain over time. In this manner, multiple receptacles can be filled and drained over time, and sensor readings from each or a group of them (e.g., all of them) can be tracked to determine fertigation fluid properties for the system 100 as a whole.

Figure 2E:
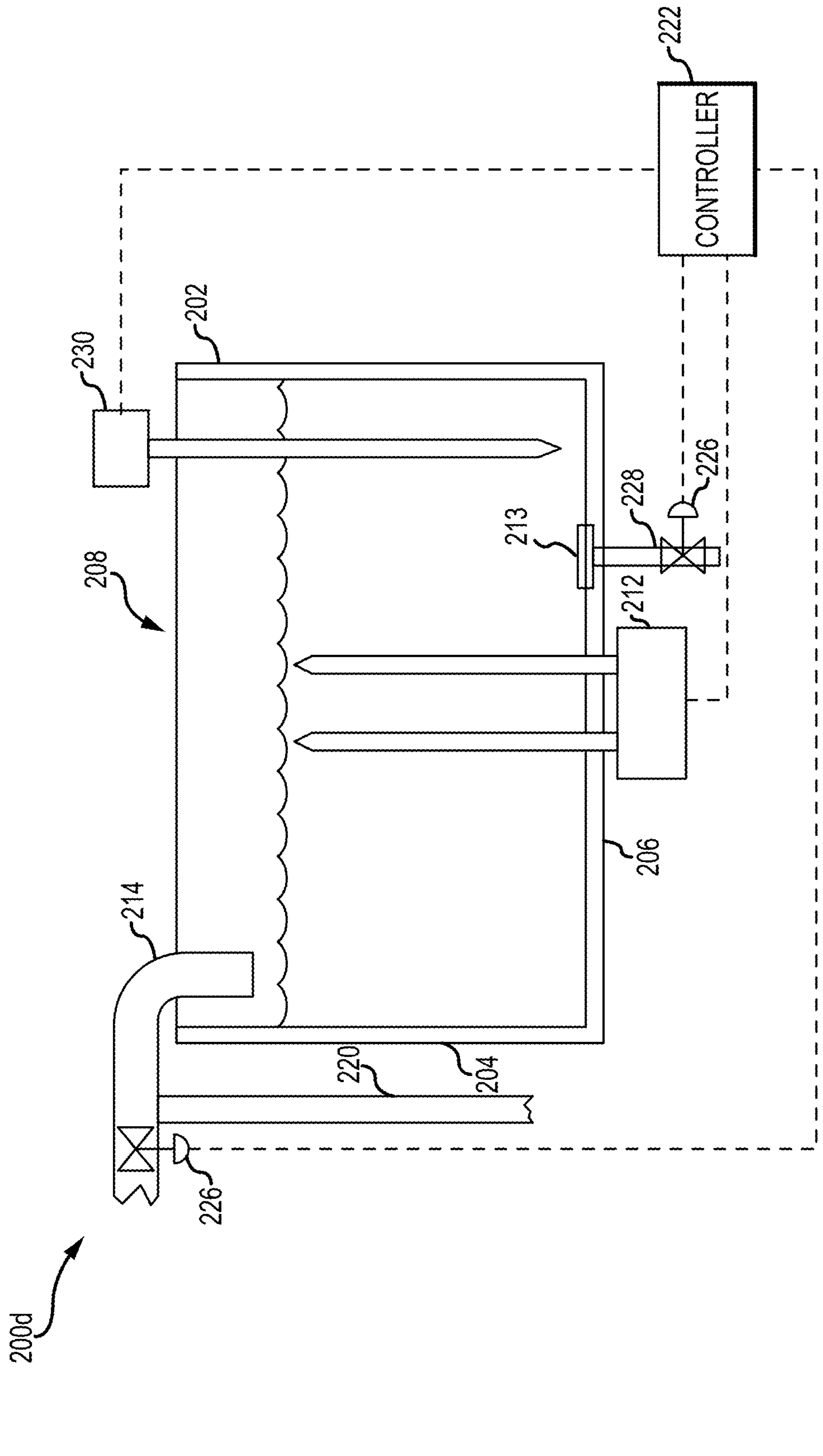
FIG. 2E is a side view of a dielectric sensor station.

FIG. 2E is a side view of a dielectric sensor station 200*d*, according to an embodiment. The dielectric sensor station 200*d* includes a receptacle 202 similar to the container of sensor station 200*a* that has a side wall 204, bottom wall 206, and opening 208. In FIG. 2E, the dielectric sensor station 200*d* is shown filled with a feed solution within the container. The dielectric sensor station 200*d* also includes a controllable drain 213. Controllable drain 213 can be a part of an automatic drainage system. The automatic drainage system can include the controllable drain 213, the sensor 212, and the feed inlet 214. In other words, the sensor 212 can be configured to produce a signal for a controller 222 configured to control the controllable drain 213 and, optionally, the feed inlet 214. In some examples, the sensor 212 can periodically take a measurement of the conductivity and/or permittivity of the solution (if any) within the receptacle 202. In some examples, the conductivity and permittivity sensor can take a reading substantially continuously or about every second, every 10 seconds, every 30 seconds, every minute, every 5 minutes, every 10 minutes, every 15 minutes, every 30 minutes, every hour, every 2 hours, or other predetermined time period as required by the fertigation system. In some examples, the sensor 212 can detect the water level in the container by sensing a different permittivity value based on the height of the solution in the container. For example, the depth in which the electrodes of the sensor 212 are submerged can directly relate to the permittivity measured by the sensor 212. When the solution has a height/depth within the container at a local maximum, or a height that covers most or all of the length (e.g., B) of the electrodes of the sensor 212, the permittivity reading may be higher than when the solution has a height/depth within the container at a local minimum, or a height that at least a portion of the electrode of the sensor 212 is not covered.

Figure 2F:
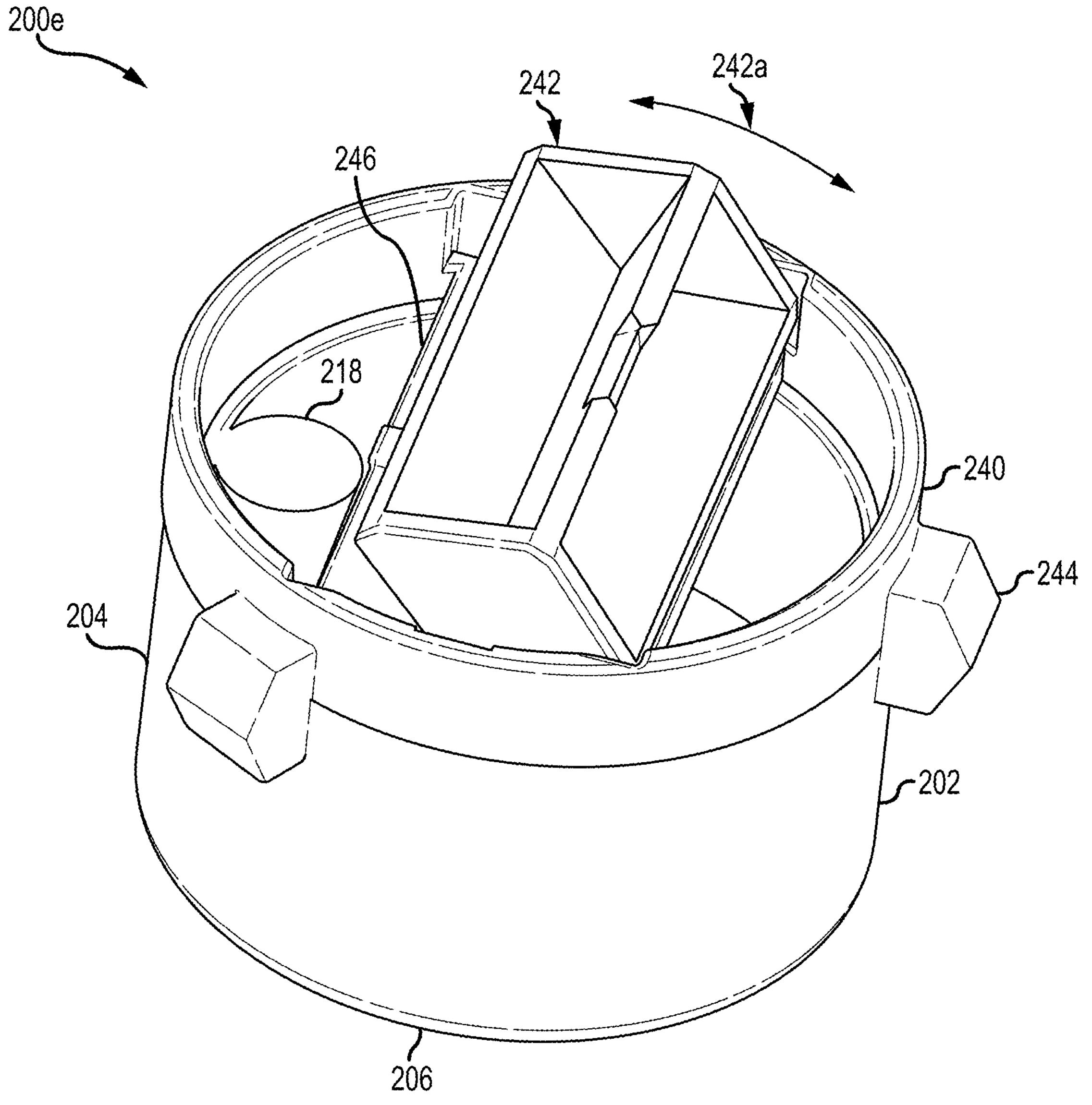
FIG. 2F is an isometric view of a dielectric sensor station.

FIG. 2F is an isometric view of a dielectric sensor station 200*e*, according to an embodiment. The dielectric sensor station 200*e* includes an attachment 240 configured to couple to the receptacle 202. The attachment 240 can include a tilting receptacle 242. The tilting receptacle 242 can function similar to the spoon receptacle 202 shown in FIG. 2D. For example, the tilting receptacle 242 includes at least one spoon container or cup configured to collect fluid and having tilting drain functionality, as represented by arrow 242*a* in FIG. 2F. Similar to the embodiment of FIGS. 2A-2E, the receptacle 242 can be automatically drained.

The attachment 240 can connect to the receptacle 202 with at least one coupling 244. For example, the coupling 244 can include a series of couplings 244 positioned around the opening of the receptacle 202 to secure the attachment 240 to the receptacle 202. The coupling 244 can connect the attachment 240 to the receptacle 202 in an interference fit, a threaded coupling, a latch, or other suitable connector. In some examples, the couplings 244 can connect the attachment 240 to the receptacle 202 permanently or removably.

In some examples, the attachment 240 can include a platform 246. The platform 246 can stabilize the attachment 240 and the tilting receptacle 242. The tilting receptacle 242 can be connected to the attachment 240 or the platform 246 with a hinge or lever at the ends of the tilting receptacle 242. Feed solution can slowly fill one of the containers of the tilting receptacle 242 from above, e.g., via inlet 214 shown in FIG. 2G. The tilting receptacle 242 uses a gravity-based tilting mechanism, wherein as the tilting receptacle 242 fills sufficiently, the weight of the feed solution within the tilting receptacle 242 causes the tilting receptacle 242 to tip and tilt downward (as indicated by arrow 242*a*) by hinging at the end hinges/levers. Thus, the feed solution pours out of the tilting receptacle 242. As shown, the tilting receptacle 242 can fill one of either of two receptacles of the tilting receptacle 242 so that the feed solution can fill and pour out of either side of the tilting receptacle 242 and into the receptacle 202.

After the feed solution sufficiently drains out of the tilting receptacle 242, it can return back to its initial position, and the feed solution can again accumulate within the receptacle 202. In practice, one of the receptacles of the tilting receptacle 242 can fill until the feed solution causes the tilting receptacle 242 to reposition and the feed solution to pour out and then the other receptacle of the tilting receptacle 242 can fill until the feed solution causes the tilting receptacle 242 to reposition and the feed solution to pour out the other side of the tilting receptacle 242. In other words, in some embodiments, the sensor station 200*e* and the tilting receptacle 242 can comprise multiple receptacles, such as, for example, two receptacles positioned on opposite sides of a pivot point, fulcrum, hinge, or lever. When the tilting receptacle 242 turns, its rotation can be limited by contact with the platform 246 so as to ensure that it does not turn beyond an angle at which the other cup will be filled. Each cup in the receptacle can be filled independently, and one cup portion can act as a counterweight for the opposite cup portion as it is filled, and the cups can alternate roles as being the filled side and the counterweight side of the tilting receptacle 242.

Figure 2G:
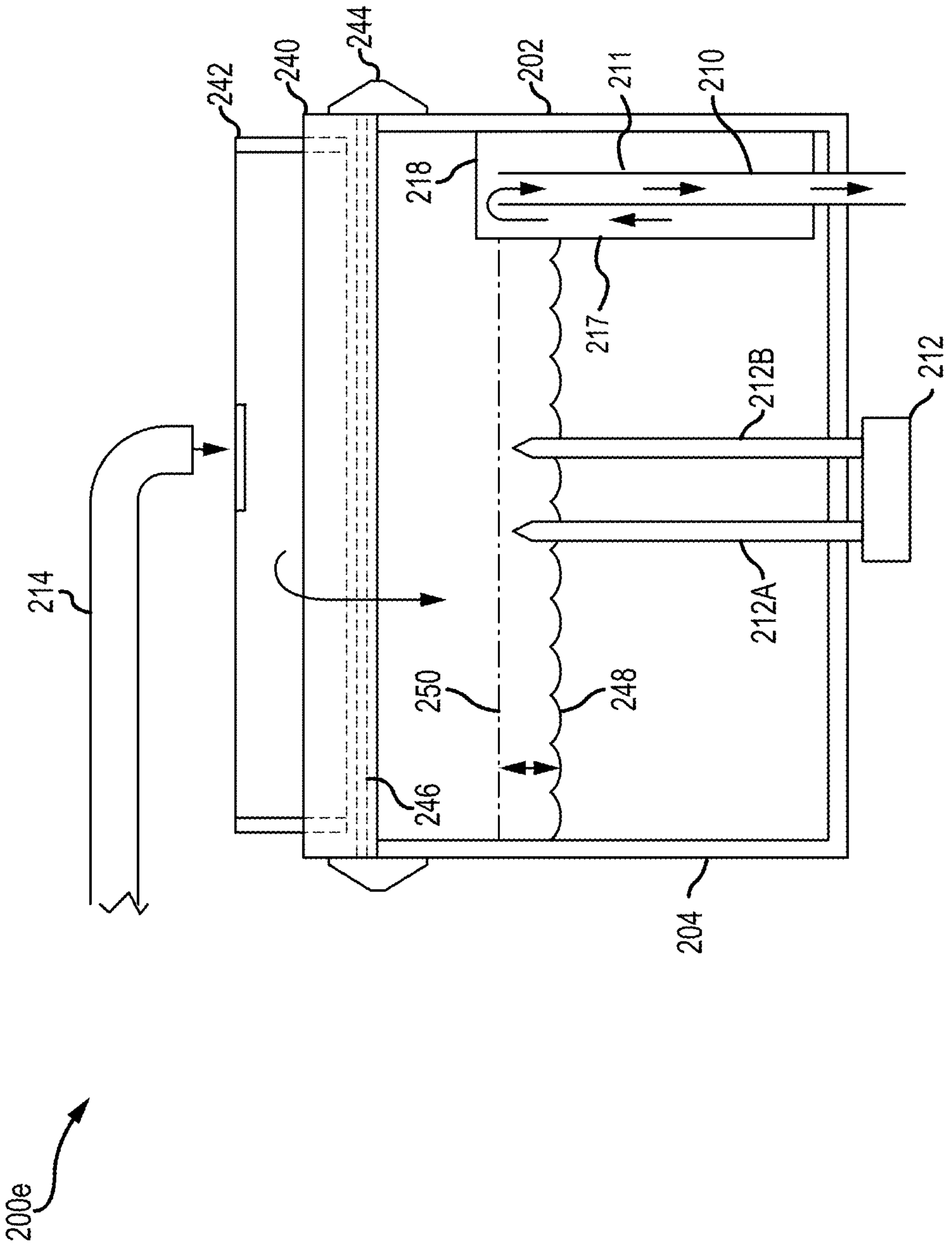
FIG. 2G is a schematic side view of the dielectric sensor station of FIG. 2F.

Referring now to FIG. 2G, which includes a side view of the dielectric sensor station 200*e*, the dielectric sensor station 200*e* can also include feed inlet 214. The feed inlet 214 can drop fluid into the tilting receptacle 242. The tilting receptacle 242 is mounted above the main receptacle 202

(e.g., a measurement receptacle or siphoned receptacle) and can be attached to the receptacle 202 with couplings 244. In some embodiments, the tilting receptacle 242 can be directly coupled with the receptacle 202 instead of by couplings 244. The platform 246 can also be directly coupled with the receptacle 202 or integrated with the receptacle 202 as a single piece. As described above, as the tilting receptacle 242 fills, the weight of the feed solution within the tilting receptacle 242 causes the tilting receptacle 242 to tip and tilt downward so that the feed solution pours out of the tilting receptacle 242 and into the lower receptacle 202. The at least two prongs 212A, 212B of the dielectric sensor station 200*e* can have respective lengths and positions relative to the tilting receptacle 242 that allow the tilting receptacle 242 to fully tilt and empty or fully fill without the tilting receptacle 242 coming into contact with the prongs. The platform 246 can ensure that the tilting receptacle 242 does not contact the prongs.

In some examples, when the tilting receptacle 242 tips, it partially fills the receptacle 202. The receptacle 202 includes the drain 210. In some examples, the drain 210 includes a siphon. The siphon can include a bell siphon similar to the bell siphon 218 as shown in FIG. 2C. The bell siphon 218 can leverage the forces of pressure and gravity, whereby as the container or receptacle 202 fills and the fluid level reaches the top of the drain standpipe 211 located inside the bell top 217 and sufficiently begins to flow through the drain standpipe 211, a low pressure area or partial vacuum will cause the feed solution to automatically flow through the siphon at the top of the drain standpipe 211 and out through the exit of the drain 210. The receptacle 202 is filled by periodic dumping of feed solution from the tilting receptacle 242. Once the feed solution within the receptacle 202 reaches a sufficient volume, the level of feed solution 248 within the receptacle 202 is increased such that a tilt of the tilting receptacle 242 adds a volume of water to suddenly increase the level of feed solution to cleanly trigger the siphon. In other words, the sudden increase of feed solution level from a first, lower level (e.g., at 248) to a new, second, higher level (e.g., at 250) can quickly exceed the elevation of the drain standpipe 211, at which time all or nearly all of the fluid in the receptacle 202 will be siphoned out of the chamber. This can help the siphon more reliably trigger as compared to embodiments where fluid enters the receptacle 202 more slowly and the siphon action is not appropriately activated.

Various other options can be used to implement an automatic drain for the sensor stations 200*a*-200*e*, such as, for example, a dripping bucket can be implemented. A pump can be provided that is controlled to periodically evacuate the fluid using a powered pumping mechanism or paddle mechanism.

Additionally, various embodiments can implement different types of depth sensors to periodically determine the amount of fluid in the receptacle and/or to detect when drainage should occur. For example, an ultrasonic depth sensor or an optical depth sensor can be used to measure fluid depth levels over time.

In some examples, the feed inlet 214 is connected to a fertigation source that includes water and fertilizer at a target ratio of concentration of water to fertilizer. The fluid flow rate of the feed inlet 214 can be designed or controlled to match the fluid flow rate to each container in a plant system connected to the source of the feed solution 102. In other words, the feed inlet 214 of one sensor system (e.g., 104) in a common fertigated zone or area can have the same volumetric flow as a feed inlet 220 that goes to a different sensor system (e.g., 106 or 108) connected to the same feed solution source. The feed solution can therefore be distributed to the first sensor system and the second sensor system via a first feed inlet and a second feed inlet configured to provide the feed solution at equal volumetric flow rates. The volumetric flow rate can be controlled by the controller 222. Generally, the controller can take periodic inputs from the sensor 212 and operate an inlet control valve 224 to control the feed inlet volumetric flow rates and an outlet control valve 226 located on a drain line 228 located downstream of the drain 213. In some examples, the level of the feed solution within the receptacle 202 can be maintained at a steady-state, consistent level as determined by the fertigation system. In other examples, the level of the feed solution within the receptacle 202 can be adjusted periodically or as determined by a conductivity/permittivity balance. In yet other examples, the level of the feed solution within the receptacle 202 can be drained completely or kept at a predetermined level as a corrective measure or as determined by the fertigation system. In some embodiments, the inlet control valve 224 can be implemented in sensor station 200*a* and can be manually or computer-controlled to manage the rate of flow into the receptacle 202 via the inlet 214.

In some examples, the dielectric sensor station 200*d*, or any of the fertigation sensor systems disclosed herein, can include a pH meter 230. In some examples, the pH meter can be positioned in the receptacle 202. In other examples, the pH meter 230 can be integrated into the other structures of the dielectric sensor station 200*d*. The ability of plants to take up some nutrients can be affected by the pH of the feed solution. It may therefore be beneficial, in some embodiments, to also monitor the pH of the solutions of the fertigation sensor systems disclosed herein. This is done by adding a pH probe in each of the sensors (e.g., 114, 116, and 118), and monitoring their outputs with the same system for monitoring and reporting the sensor systems. In other words, the controller 22 can also receive a signal from the pH meter, and the fertigation system can be controlled according to the pH of the feed solution within the receptacle 202.

Figure 3:
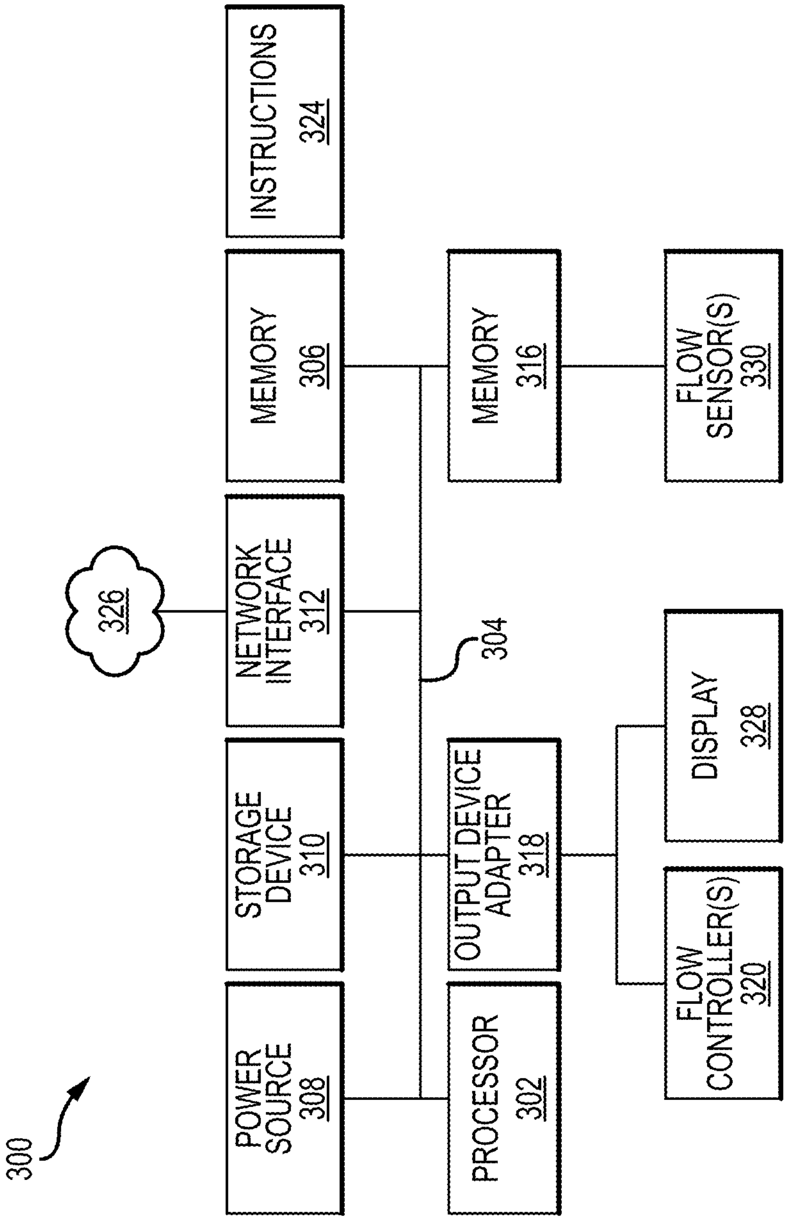
FIG. 3 is a block flow diagram for a controller system operationally connected to the fertigation sensor system.

FIG. 3 is a high-level block diagram of a computer system 300 for a controller system operationally connected to the fertigation sensor system, according to an embodiment. As used herein, parts in "electrical communication" with each other are configured to exchange electrical signals, directly or indirectly, between each other, whether unidirectionally or bidirectionally. A flow sensor (e.g., 330) can be in electrical communication with a processor 302 or flow controller 320 if the processor 302 or flow controller 320 is using signals generated by the flow sensor 330 or if the processor 302 or flow controller 320 is using signals reliant upon or derived at least in part on the signals generated by the flow sensor 330. For example, the flow sensor 330 can be in electrical communication with a processor 302 via an input device adapter 316 and an electrical communications bus 304, as indicated in FIG. 3 and described in further detail below.

In various embodiments, the computer system 300 can comprise various sets and subsets of the components shown in FIG. 3. Thus, FIG. 3 shows a variety of components that can be included in various combinations and subsets based on the operations and functions performed by the system 300 in different embodiments. For example, the computer system 300 can be embodied as controller 120 and/or as part of the first sensor system 104, second sensor system 106, third sensor system 108, and dielectric sensor stations 200*a*-200*e* described above in connection with FIGS. 1 and 2A-2G.

The computer system 300 can comprise a central processing unit (CPU) or processor 302 connected via a bus 304 for electrical communication to a memory device 306, a power source 308, an electronic storage device 310, a network interface 312, an input device adapter 316, and an output device adapter 318. For example, one or more of these components can be connected to each other via a substrate (e.g., a printed circuit board or other substrate) supporting the bus 304 and other electrical connectors providing electrical communication between the components." The bus 304 can comprise a communication mechanism for communicating information between parts of the system 300.

The processor 302 can be a microprocessor or similar device configured to receive and execute a set of instructions 324 stored by the memory 306. The memory 306 can be referred to as main memory, such as random access memory (RAM) or another dynamic electronic storage device for storing information and instructions to be executed by the processor 302. The memory 306 can also be used for storing temporary variables or other intermediate information during execution of instructions executed by the processor 302. The processor 302 can include or implement one or more processors or controllers, such as, for example, the controller 222 of FIG. 2E or controller 120 of FIG. 1. The power source 308 can comprise a power supply capable of providing power to the processor 302 and other components connected to the bus 304, such as a connection to an electrical utility grid or a battery system.

The storage device 310 can comprise read-only memory (ROM) or another type of static storage device coupled to the bus 304 for storing static or long-term (i.e., non-dynamic) information and instructions for the processor 302. For example, the storage device 310 can comprise a magnetic or optical disk (e.g., hard disk drive (HDD)), solid state memory (e.g., a solid state disk (SSD)), or a comparable device.

The instructions 324 can comprise information for executing processes and methods using components of the system 300. Such processes and methods can include, for example, the methods described in connection with other embodiments elsewhere herein, including, for example, the methods and processes described in connection with FIGS. 1, 2A-2G, and 4.

The network interface 312 can comprise an adapter for connecting the system 300 to an external device via a wired or wireless connection. For example, the network interface 312 can provide a connection to a computer network 326 such as a cellular network, the Internet, a local area network (LAN), a separate device capable of wireless communication with the network interface 312, other external devices or network locations, and combinations thereof. In one example embodiment, the network interface 312 is a wireless networking adapter configured to connect via WI-FI®, BLUETOOTH®, BLE, Bluetooth mesh, or a related wireless communications protocol to another device having interface capability using the same protocol. In some embodiments, a network device or set of network devices in the network 326 can be considered part of the system 300. In some cases, a network device can be considered connected to, but not a part of, the system 300.

The input device adapter 316 can be configured to provide the system 300 with connectivity to various input devices such as, for example, one or more flow sensors 330 (e.g., sensors 114, 116, 118), related devices, and combinations thereof. In an example embodiment, the input device adapter 316 is connected to the pH meter 230 to determine the pH of the solution within a receptacle of the fertigation sensor. The sensors 330 can be used to detect physical phenomena in the vicinity of the computing system 300 (e.g., conductivity, permittivity, pH, temperature, etc.) and convert those phenomena to electrical signals. In some examples, a keyboard or another input device (e.g., buttons or switches) can be used to provide user input to the processor, such as input regarding the settings of the system 300.

The output device adapter 318 can be configured to provide the system 300 with the ability to output information to a user, such as by providing visual output using one or more displays 328. The processor 302 can be configured to control the output device adapter 318 to provide information to a user via the output devices connected to the adapter 318. In some embodiments, the processor 302 and/or output device adapter 318 can be used to filter, curve-fit, interpolate, or smooth input provided to the flow sensor(s) 330.

Figure 4:
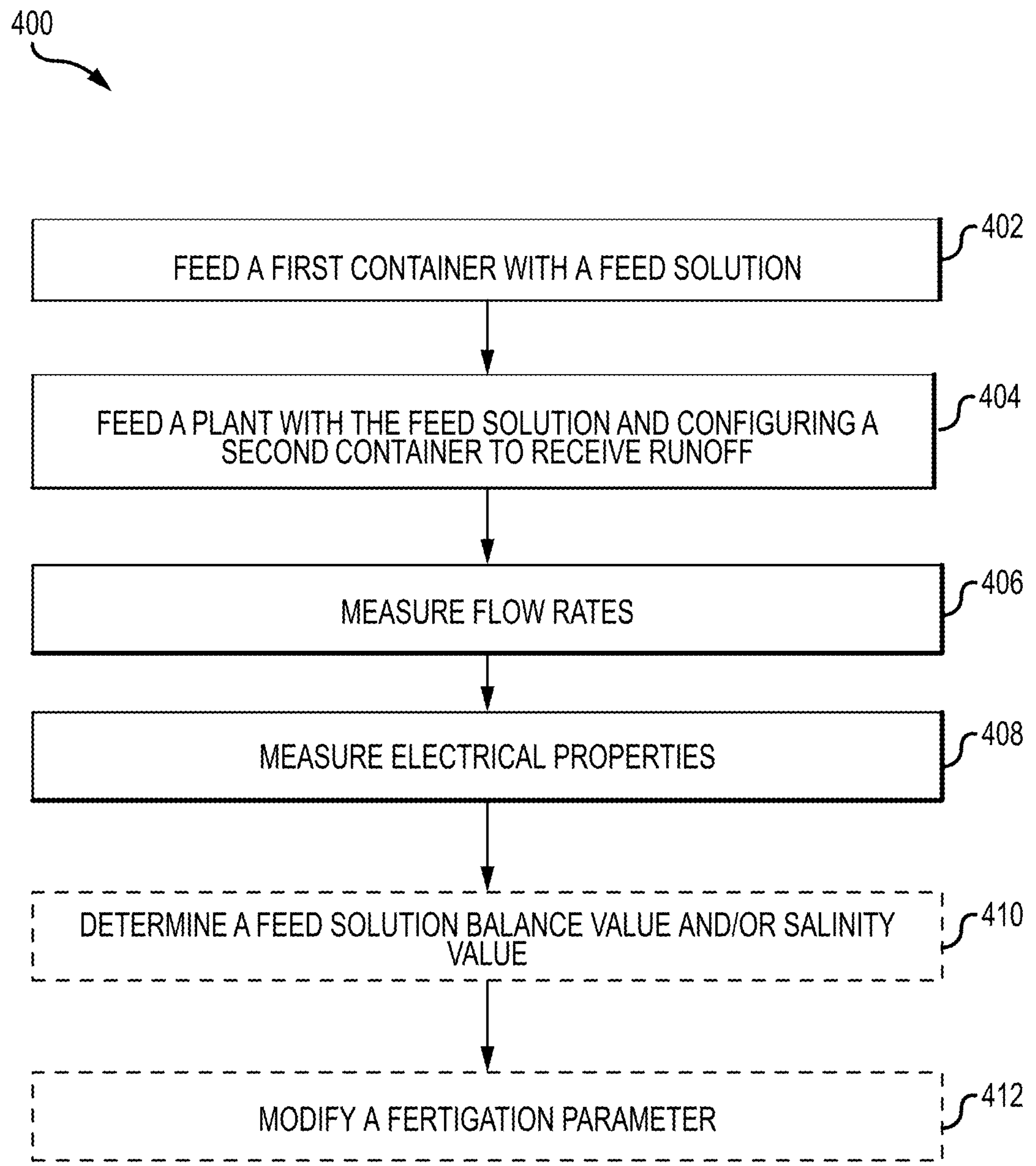
FIG. 4 is a block flow diagram for a method of determining a fertigation feed properties.

FIG. 4 is a flow diagram of a method 400 for determining and controlling fertigation feed properties. The method 400 for determining fertigation feed properties may utilize use any of the fertigation sensor systems, dielectric sensor stations, and/or assemblies disclosed herein. The method 400 may include block 402, which includes establishing a feed sensor system by feeding a first container with a feed solution, e.g., feed solution 102, that includes water and fertilizer at a target ratio of concentration of water to fertilizer, wherein the first container comprises a feed sensor such as, for example, a sensor 114 or 212 described herein. Block 402 may be followed by block 404, which includes establishing a runoff sensor system by feeding a plant substrate or plant container with the feed solution and configuring a second container to receive runoff from the plant container, wherein the second container comprises a runoff sensor such as, for example, a sensor 116, 118, or 212 described herein. Thus, by completing blocks 402 and 404, a fertigation system 100 can be organized, assembled, and prepared for operation.

Blocks 402 and 404 of the method 400 are shown for illustrative purposes. For example, all acts or blocks illustrated of the method 400 may be performed in different orders, split into multiple acts, modified, supplemented, or combined. In an example, one or more of the acts of the method 400 may be omitted from the method 400. Any of the acts of the method 400 can include using any of the fertigation sensor assemblies or systems disclosed herein.

Block 406 includes measuring a volumetric flow rate of the feed solution at the first container and the volumetric flow rate of the runoff into the second container. This may include utilizing any of the sensor systems disclosed herein or other sensor systems and sensors known in the art. In some embodiments, the flow rate can be determined based on a rate of drainage events detected by the sensor (e.g., sensor 212). For example, as the sensor 212 periodically measures permittivity of fluid in a container, e.g., every few seconds or minutes, as described above, the measurements, when tracked over time, can indicate highs and lows in the electrical permittivity correlating to the highs and lows in the fluid level in the container as it is filled and automatically drained. When the permittivity measurement transitions from a high to a low value, a drainage event can be identified and recorded. The number of these events can be tracked over time and associated with the volume of fluid that would be automatically drained in each event, thereby producing the volumetric flow rate of fluid passing through the container. Thus, in some examples, block 406 may include periodically draining the first container and tracking drainage events over time. In some examples, the first container can be drained automatically using a drain system (e.g., 213/226/228). In other examples, the drain can include a siphon (e.g., 210).

At block 408, the method 400 may include measuring at least one electrical property (e.g., conductivity and/or permittivity) of the feed solution with the feed sensor and at least one electrical property (e.g., conductivity and/or permittivity) of the runoff with the runoff sensor. The electrical property measured for the feed solution can be the same type of electrical property measured for the runoff so as to enable a comparison of any changes between the electrical properties before being provided to the plant/substrate (i.e., the initial feed solution) and after being provided to the plant/substrate (i.e., the runoff solution). In some embodiments, the conductivity can be measured with a sensor (e.g., 114) disposed within the first container and a sensor (e.g., 116) disposed within the second container.

In some examples, measuring the electrical conductivity and/or permittivity of the feed solution with the feed sensor can include identifying a measurement of the conductivity and/or permittivity in the first container where and when the feed solution reaches a local maximum. In some embodiments, the method 400 can include identifying a series or plurality of local maxima across a span or duration of time. The local maximum (or maxima) can be identified within specified durations of time, such as a maximum conductivity or permittivity value measured between detected drainage events (i.e., changes from maximum to minimum), wherein the local maximum can be detected as the highest permittivity value immediately preceding the automatic drainage event. To illustrate, the electrical permittivity of a feed solution in a receptacle can be measured at predetermined intervals (e.g., every few seconds, minutes, etc., as described above), and the receptacle can complete one cycle of drainage to slowly refilling to drainage again over a cycle time duration. In an example, the cycle time duration can be 30 to 60 minutes. (However, more or less time in a cycle is contemplated since the cycle time duration is dependent on the flow rate at which feed solution is provided and the overall volume within the receptacle.) Thus, for every 30 to 60 minutes (or other cycle time duration), a local maximum electrical permittivity can be identified in connection with block 408.

The conductivity and permittivity measurements will be at a local maximum when the electrodes are nearly or entirely submerged. Thus, a local maximum measurement of the conductivity and permittivity in a container can correspond to conditions including a filled or substantially filled receptacle (i.e., the solution is at or near its maximum level before being automatically drained) and nearly or entirely submerged electrodes. Thus, a local maximum conductivity can be identified to determine feed solution component properties such as the relative concentrations of fertilizers and other chemicals to water.

In some examples, the method 400 can optionally further include block 410 and block 412. In block 410 the method 400 can further include determining, for the feed solution and the runoff solution, at least one of: a feed solution balance value or a salinity value. Plant analysis can provide a nutrient content of the biomass. In some examples, the method of determining a fertigation feed properties includes computing the nutrients needed in the irrigation water to meet the growth demands of the crop and/or plant(s). The amounts can vary, depending on the plant and its environment, so the sensors can provide measurements that can further be used to calculate the proper water to fertilizer ratios and provide a feed solution balance value or a salinity value to determine the proper fertilizer and water amounts are and that they are being correctly supplied. A dielectric sensor can monitor the volume of the feed solution (corresponding to the flow rate over time and permittivity of the solution) and the electrical conductivity of the feed solution applied to a plant system, and the system can monitor the volume and the electrical conductivity of the feed solution draining from the plant (i.e., the runoff or leachate). With the volume and electrical conductivity of the feed solution draining from the plant, the feed solution balance and salinity balance for the plant is determined, allowing the irrigator to know how much feed solution to apply and what concentration of nutrient solution to apply so that plant needs are fully met, and water or nutrients waste is minimized or eliminated.

In block 412, the method 400 can further include modifying fertigation parameters based on the volumetric flow rate and the conductivity measurements. In some examples, flow can be controlled so that equal volumes of feed solution are distributed to each plant and/or each plant system. In some examples, the height of the feed solution in the container is determined from the permittivity of the solution and is monitored and recorded, along with the electrical conductivity. Volume of feed solution can be computed from the recorded height. The difference between applied feed solution and drainage is the transpiration and/or evaporation of the plant system. The volume of feed solution, multiplied by a concentration of nutrients in the feed solution, can determine the amount of nutrients applied. The volume of drainage, multiplied by the concentration of nutrients in the drainage, is the amount of nutrients lost from the system. The difference is the amount of nutrients taken up by the plant (assuming there is a long enough averaging time so changes in the feed solution and nutrient storage in the soil can be neglected). Thus, fertigation parameters such as the flow rate of feed solution, the frequency or timing of irrigation, the concentrations of fertilizers in the feed solution, the types of fertilizers provided in the feed solution, other fertigation parameters, and combinations thereof can be adjusted based on the flow rate and electrical conductivity and permittivity parameters. In some cases, the parameters can be adjusted based on grower experience, cost management requirements, or similar factors. In some embodiments, an algorithm or model can be applied using the flow rate and conductivity measurements to optimize and improve plant uptake and growth, to minimize waste, and to improve crop efficiency and harvests. A different algorithm or model can be developed and applied to various plant species, growing conditions (e.g., grow lighting types, plant density, substrate properties, etc.), fertilizer types, desired growth rates, desired failure rates, and similar concerns. Thus, sensor systems disclosed herein can provide a low cost solution (only requiring two sensors at minimum) for management and development of data-driven fertigation control and crop management procedures.

While various aspects and embodiments have been disclosed herein, other aspects and embodiments are contemplated. The various aspects and embodiments disclosed herein are for purposes of illustration and are not intended to be limiting.

Terms of degree (e.g., "about," "substantially," "generally," etc.) indicate structurally or functionally insignificant variations. In an example, when the term of degree is included with a term indicating quantity, the term of degree is interpreted to mean ±10%, ±5%, or ±2% of the term indicating quantity. Further, the terms "less than," "or less," "greater than," "more than," or "or more" include, as an endpoint, the value that is modified by the terms "less than," "or less," "greater than," "more than," or "or more." In an example, when the term of degree is used to modify a shape, the term of degree indicates that the shape being modified by the term of degree has the appearance of the disclosed shape. For instance, the term of degree may be used to indicate that the shape may have rounded corners instead of sharp corners, curved edges instead of straight edges, one or more protrusions extending therefrom, is oblong, is the same as the disclosed shape, etc.

As used herein, conjunctive terms (e.g., "and") and disjunctive terms (e.g., "or") should be read as being interchangeable (e.g., "and/or") whenever possible. Furthermore, in claims reciting a selection from a list of elements following the phrase "at least one of," usage of "and" (e.g., "at least one of A and B") requires at least one of each of the listed elements (i.e., at least one of A and at least one of B), and usage of "or" (e.g., "at least one of A or B") requires at least one of any individual listed element (i.e., at least one of A or at least one of B). It is noted that, when described or recited herein, the use of the articles such as "a" or "an" is not considered to be limiting to only one, but instead is intended to mean one or more unless otherwise specifically noted herein.

What is claimed is:

1. A fertigation sensor system, comprising:
a first sensor system including:
a first container configured to directly collect a feed solution originating from a fertigation source, the feed solution comprising water and fertilizer at a target ratio of concentration of water to fertilizer; and
a first sensor disposed in the first container;
a plant container configured to be directly provided the feed solution from the fertigation source via an outlet separate from the first container; and
a second sensor system comprising:
a second container configured to collect leachate from the plant container of the feed solution originating from the fertigation source; and
a second sensor disposed in the second container.

2. The system of claim 1, wherein the feed solution is distributed to the first sensor system and to the second sensor system from the fertigation source via a first feed inlet and a second feed inlet, wherein the first feed inlet and the second feed inlet are configured to provide the feed solution at equal volumetric flow rates.

3. The system of claim 2, wherein the first feed inlet and the second feed inlet have a same target ratio of concentration of water to fertilizer.

4. The system of claim 1, wherein the first sensor comprises an electrical conductivity and permittivity sensor having at least one prong positioned extending upward from a bottom wall of the first container.

5. The system of claim 4, wherein the at least one prong includes two electrodes spaced apart from each other within the first container.

6. The system of claim 5, wherein the two electrodes are laterally spaced apart from each other.

7. The system of claim 1, wherein the first container comprises a first automatic drainage system and the second container comprises a second automatic drainage system.

8. A sensor station, comprising:
a receptacle configured to hold a feed solution;
a conductivity and permittivity sensor comprising at least two prongs disposed in the receptacle; and
a drain configured to substantially empty the receptacle by removing the feed solution from the receptacle in response to a predetermined amount of feed solution being present in the receptacle.

9. The sensor station of claim 8, wherein the drain comprises a siphon.

10. The sensor station of claim 8, wherein the conductivity and permittivity sensor is connected to a controller configured to periodically measure and record conductivity and permittivity of the feed solution.

11. The sensor station of claim 8, wherein the at least two prongs extend from a bottom surface of the receptacle.

12. The sensor station of claim 8, wherein the at least two prongs comprise electrodes that terminate at or below a top of a solution receiving chamber defined in the receptacle.

13. The sensor station of claim 8, further comprising a pH probe disposed in the receptacle.

14. A method of determining a fertigation feed properties, the method comprising:
establishing a feed sensor system by feeding a first container with a feed solution that includes water and fertilizer at a target ratio of concentration of water to fertilizer, the first container comprising a feed sensor;
establishing a runoff sensor system by feeding a plant container with the feed solution and configuring a second container to receive runoff from the plant container, the second container comprising a runoff sensor;
measuring a volumetric flow rate of the feed solution and the runoff, wherein measuring the volumetric flow rate includes automatically draining the first container via a drain substantially emptying the first container when a predetermined amount of the feed solution is present in the first container; and
measuring electrical properties of the feed solution with the feed sensor and electrical properties of the runoff with the runoff sensor.

15. The method of claim 14, further comprising determining, for the feed solution and the runoff, at least one of: a feed solution balance value or a salinity value.

16. The method of claim 14, wherein measuring a volumetric flow rate of the feed solution comprises periodically draining the first container and tracking drainage events over time.

17. The method of claim 16, wherein tracking drainage events comprises measuring the electrical properties in the first container and correlating the electrical properties to a fluid level in the first container.

18. The method of claim 14, wherein measuring electrical properties of the feed solution comprises measuring at least the electrical conductivity and the permittivity of the feed solution with the feed sensor.

19. The method of claim 14, further comprising modifying fertigation parameters based on measurements of the volumetric flow rate and the electrical properties.

* * * * *